US012797325B2

(12) United States Patent
Almeida

(10) Patent No.: US 12,797,325 B2
(45) Date of Patent: Nov. 17, 2026

(54) AMINOSILOXANE/ALKYL SILANE BLEND

(71) Applicant: Dow Global Technologies LLC, Midland, MI (US)

(72) Inventor: Daniel Almeida, Paulinia (BR)

(73) Assignee: Dow Global Technologies LLC, Midland, MI (US)

( * ) Notice: Subject to any disclaimer, the term of this patent is extended or adjusted under 35 U.S.C. 154(b) by 1490 days.

(21) Appl. No.: 17/432,673

(22) PCT Filed: Apr. 6, 2020

(86) PCT No.: PCT/US2020/026812

§ 371 (c)(1),
(2) Date: Aug. 20, 2021

(87) PCT Pub. No.: WO2020/214442

PCT Pub. Date: Oct. 22, 2020

(65) Prior Publication Data

US 2022/0175653 A1 Jun. 9, 2022

Related U.S. Application Data

(60) Provisional application No. 62/835,666, filed on Apr. 18, 2019.

(51) Int. Cl.
*A61K 8/898* (2006.01)
*A61K 8/58* (2006.01)
*A61Q 5/12* (2006.01)

(52) U.S. Cl.
CPC .............. *A61K 8/898* (2013.01); *A61K 8/585* (2013.01); *A61Q 5/12* (2013.01)

(58) Field of Classification Search
CPC .......... A61Q 5/12; A61Q 5/002; A61K 8/898; A61K 8/585; A61K 8/28; A61K 8/891; A61K 8/29
See application file for complete search history.

(56) References Cited

U.S. PATENT DOCUMENTS

| | | | |
|---|---|---|---|
| 4,344,763 | A | 8/1982 | Ann et al. |
| 6,352,699 | B1 | 3/2002 | Mondet et al. |
| 2008/0172807 | A1 | 7/2008 | Brun et al. |

FOREIGN PATENT DOCUMENTS

| | | | | | |
|---|---|---|---|---|---|
| EP | 0113992 | | | 7/1984 | |
| EP | 0113992 | A1 | * | 7/1984 | ............. A61K 8/898 |
| WO | 2007007279 | | | 1/2007 | |
| WO | WO2008148809 | A1 | * | 12/2008 | ............... A61K 8/86 |
| WO | WO2018186138 | A1 | * | 10/2018 | |

OTHER PUBLICATIONS

WO2018186138A1, Google English Translation document, downloaded in Mar. 2025 (Year: 2025).*
Universal Selector, Xiameter™ OFS-6106 Silane, Technical DataSheet, Supplied by Dow, last edited date: Sep. 9, 2024 (Year: 2024).*
Office Action from corresponding Chinese Application No. 202080021361.8 dated Nov. 24, 2023.

* cited by examiner

*Primary Examiner* — Mark V Stevens
*Assistant Examiner* — Arya Ahmadi Bazargani
(74) *Attorney, Agent, or Firm* — Thomas S. Deibert

(57) ABSTRACT

An aminosiloxane/alkyl silane blend for imparting hydrophobicity to hair, comprising: 0.2 to 15 wt % of a cosmetically acceptable condensation catalyst selected from the group consisting of organic titanates, organic zirconates and mixtures thereof; 1 to 20 wt % of a cosmetically acceptable aminosiloxane of formula (I); 5 to 75 wt % of a cosmetically acceptable alkyl silane of formula (II); and 15 to 93.8 wt % of a cosmetically acceptable polydimethylsiloxane of formula (III).

10 Claims, No Drawings

AMINOSILOXANE/ALKYL SILANE BLEND

The present invention relates to an aminosiloxane/alkyl silane blend for imparting hydrophobicity to hair. In particular, the present invention relates to an aminosiloxane/alkyl silane blend for imparting hydrophobicity to hair, comprising: 0.2 to 15 wt % of a cosmetically acceptable condensation catalyst selected from the group consisting of organic titanates, organic zirconates and mixtures thereof; 1 to 20 wt % of a cosmetically acceptable aminosiloxane of formula (I); 5 to 75 wt % of a cosmetically acceptable alkyl silane of formula (II); and 15 to 93.8 wt % of a cosmetically acceptable polydimethylsiloxane of formula (III).

Undamaged hair tends to be smooth and shiny and hydrophobic in nature preventing excessive water adsorption during washing. Once hair is damaged either mechanically or chemically (i.e., through bleaching, perming or coloring), the hair surface becomes more hydrophilic. As the hair surface becomes more hydrophilic, the resulting hair fibers tend to swell during washing making the hair more difficult to manage (e.g., comb).

There is an increasing demand for hair care products designed to retain the properties of undamaged hair and to help prevent damage.

There remains a continuing need for additives and blends for use in personal care formulations (in particular hair care formulations) that impart hydrophobicity to hair.

The present invention provides a aminosiloxane/alkyl silane blend for imparting hydrophobicity to hair, comprising: (a) 0.2 to 15 wt % of a cosmetically acceptable condensation catalyst selected from the group consisting of organic titanates, organic zirconates and mixtures thereof; (b) 1 to 20 wt % of a cosmetically acceptable aminosiloxane of formula (I)

(I)

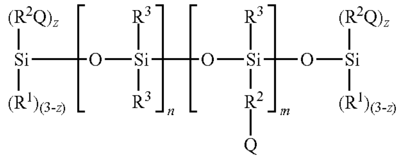

wherein each $R^1$ is independently selected from the group consisting of a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group; wherein $R^2$ is a divalent alkylene radical having one to ten carbon atoms; wherein each $R^3$ is independently selected from the group consisting of a $C_{1-30}$ alkyl group, a $C_{5-30}$ aryl group, a $C_{6-30}$ aralkyl group and a $C_{1-30}$ alkaryl group; wherein Q is a monovalent radical selected from the group consisting of $—NR^4_2$ and $—NR^4(CH_2)_xNR^4_2$; wherein each $R^4$ is independently selected from the group consisting of a hydrogen and a $C_{1-4}$ alkyl group; wherein x is 2 to 6; wherein z is 0 or 1; wherein n is 25 to 3,000 and wherein m is 0 to 3,000; with the proviso that at least 50 mol % of the total number of $R^1$ and $R^3$ groups are methyl and with the proviso that when m is 0, z is 1; (c) 5 to 75 wt % of a cosmetically acceptable alkyl silane of formula (II)

(II)

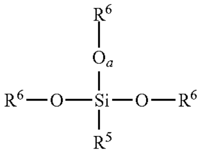

wherein a is selected from 0 and 1; wherein $R^5$ is a $C_{2-10}$ alkyl group with an addition reaction functional moiety and wherein each $R^6$ is independently selected from a $C_{1-4}$ alkyl group; and (d) 15 to 93.8 wt % of a cosmetically acceptable polydimethylsiloxane of formula (III)

(III)

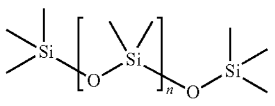

wherein n is an average of 0 to 150.

DETAILED DESCRIPTION

We have now surprisingly found that the identified unique blend of four components provides exemplary persistent hydrophobicity to damaged hair, wherein the treated hair exhibits continued enhanced hydrophobicity after as many as thirty subsequent washes.

Unless otherwise indicated, ratios, percentages, parts, and the like are by weight.

The term "cosmetically acceptable" as used herein and in the appended refers to ingredients typically used in personal care compositions, and is intended to underscore that materials that are toxic when present in the amounts typically found in personal care compositions are in hair care compositions are not contemplated as part of the present invention.

Preferably, the aminosiloxane/alkyl silane blend for imparting hydrophobicity to hair of the present invention, comprises: (a) 0.2 to 15 wt % (preferably, 0.5 to 10 wt %; more preferably, 1 to 8 wt %) of a cosmetically acceptable condensation catalyst selected from the group consisting of organic titanates, organic zirconates and mixtures thereof; (b) 1 to 20 wt % (preferably, 1.5 to 17 wt %; more preferably, 2 to 15 wt %) of a cosmetically acceptable aminosiloxane of formula (I)

(I)

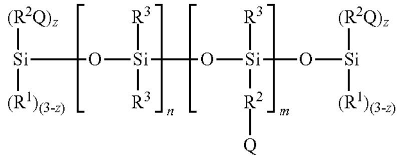

wherein each $R^1$ is independently selected from the group consisting of a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group; wherein $R^2$ is a divalent alkylene radical having one to ten carbon atoms (preferably, three to six carbon atoms); wherein each $R^3$ is independently selected from the group consisting of a $C_{1-30}$ alkyl group, a $C_{5-30}$ aryl group, a $C_{6-30}$ aralkyl group and a $C_{1-30}$ alkaryl group; wherein Q is a monovalent radical selected from the group consisting of $—NR^4_2$ and $—NR^4(CH_2)_xNR^4_2$; wherein each $R^4$ is independently selected from the group consisting of a hydrogen and a $C_{1-4}$ alkyl group; wherein x is 2 to 6; wherein z is 0 or 1; wherein n is 25 to 3,000 (preferably, 25 to 2,000; more preferably, 25 to 1,000; most preferably 25 to 500) and wherein m is 0 to 3,000 (preferably, 0 to 2,000; more preferably, 0 to 1,000; most preferably, 0 to 100); with the proviso that at least 50 mol % of the total number of $R^1$ and $R^3$ groups are methyl and with the proviso that when m is 0, z is 1; (c) 5 to 75 wt % (preferably, 10 to 70 wt %; more preferably, 40 to 60 wt %) of a cosmetically acceptable alkyl silane of formula (II)

(II)

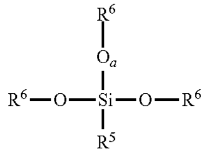

wherein a is selected from 0 and 1 (preferably, wherein a is a 1); wherein $R^5$ is a $C_{2-10}$ alkyl group with an addition reaction functional moiety; and wherein each $R^6$ is independently selected from a $C_{1-4}$ alkyl group; and (d) 15 to 93.8 wt % (preferably, 20 to 88 wt %; more preferably, 25 to 57 wt %) of a cosmetically acceptable polydimethylsiloxane of formula (III)

(III)

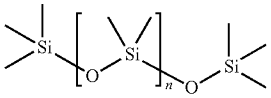

wherein n is an average of 0 to 150 (preferably, 0 to 100; more preferably, 0 to 50; still more preferably, 0 to 25; most preferably, 0 to 8).

Preferably, the aminosiloxane/alkyl silane blend for imparting hydrophobicity to hair of the present invention, comprises a cosmetically acceptable condensation catalyst selected from the group consisting of organic titanates, organic zirconates and mixtures thereof. More preferably, the aminosiloxane/alkyl silane blend for imparting hydrophobicity to hair of the present invention, comprises 0.2 to 15 wt % (preferably, 0.5 to 10 wt %; more preferably, 1 to 8 wt %) of a cosmetically acceptable condensation catalyst selected from the group consisting of organic titanates, organic zirconates and mixtures thereof. Most preferably, the aminosiloxane/alkyl silane blend for imparting hydrophobicity to hair of the present invention, comprises 0.2 to 15 wt % (preferably, 0.5 to 10 wt %; more preferably, 1 to 8 wt %) of a cosmetically acceptable condensation catalyst, wherein the cosmetically acceptable condensation catalyst includes an organic titanate (preferably, a tetra-n-butyl titanate).

Preferably, the organic titanate and organic zirconate based catalysts from which the cosmetically acceptable condensation catalyst is selected comprise compounds according to the general formula $M[OR]_4$; wherein M is selected from the group consisting of Ti and Zr (preferably, Ti) and wherein each R is independently selected from a monovalent, primary, secondary or tertiary aliphatic hydrocarbon group which can be linear or branched containing 1 to 10 carbon atoms. Preferably, each R is independently selected from the group consisting of a methyl group, an ethyl group, a propyl group, an isopropyl group, a butyl group, a tertiary butyl group and a branched secondary alkyl group (e.g., 2,4-dimethyl-3-pentyl). More preferably, all the R's are the same. Yet more preferably, all the R's are the same and are selected from n-butyl, t-butyl, butyl and isopropyl. Most preferably, all the R's are the same and are n-butyl.

Preferably, the aminosiloxane/alkyl silane blend for imparting hydrophobicity to hair of the present invention, comprises a cosmetically acceptable aminosiloxane of formula (I). More preferably, the aminosiloxane/alkyl silane blend for imparting hydrophobicity to hair of the present invention, comprises 1 to 20 wt % (preferably, 1.5 to 17 wt %; more preferably, 2 to 15 wt %) of a cosmetically acceptable aminosiloxane of formula (I)

(I)

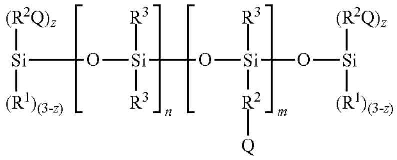

wherein each $R^1$ is independently selected from the group consisting of a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, wherein each $R^1$ is independently selected from the group consisting of a $C_{1-30}$ alkyl group, a $C_{1-30}$ alkoxy group and a hydroxy group); wherein $R^2$ is a divalent alkylene radical having one to ten carbon atoms (preferably, wherein $R^2$ is a divalent alkylene radical having three to six carbon atoms); wherein each $R^3$ is independently selected from the group consisting of a $C_{1-30}$ alkyl group, a $C_{5-30}$ aryl group, a $C_{6-30}$ aralkyl group and a $C_{1-30}$ alkaryl group (preferably, wherein each $R^3$ is independently selected from the group consisting of a $C_{1-30}$ alkyl group); wherein Q is a monovalent radical selected from the group consisting of $—NR^4_2$ and $—NR^4(CH_2)_xNR^4_2$; wherein each $R^4$ is independently selected from the group consisting of a hydrogen and a $C_{1-4}$ alkyl group; wherein x is 2 to 6; wherein z is 0 or 1; wherein n is 25 to 3,000 (preferably, 25 to 2,000; more preferably, 25 to 1,000; most preferably 25 to 500) and wherein m is 0 to 3,000 (preferably, 0 to 2,000; more preferably, 0 to 1,000; most preferably, 0 to 100); with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy.

Preferred $R^2$ divalent alkylene radicals include trimethylene, tetramethylene, pentamethylene, $—CH_2CH(CH_3)CH_2—$ and $—CH_2CH_2CH(CH_3)CH_2—$.

Preferred $R^3$ groups include methyl, ethyl, propyl, isopropyl, butyl, isobutyl, phenyl, xenyl, benzyl, phenylethyl and tolyl.

Preferred $R^4$ groups include methyl, ethyl, propyl, isopropyl, butyl and isobutyl.

When z is 0, the cosmetically acceptable aminosiloxane has only pendant amine functional substituents in the polymer chain. When z is 1, the cosmetically acceptable aminosiloxane may have only terminal amine functional substituents (e.g., m=0) or may have both terminal and pendant amine functional substituents in the polymer chain (e.g., m>0).

Preferably, n+m is 50 to 1,000. More preferably, n+m is 50 to 750. Still more preferably, n+m is 50 to 500. Most preferably, n+m is 50 to 250.

Preferably, the aminosiloxane/alkyl silane blend for imparting hydrophobicity to hair of the present invention, comprises a cosmetically acceptable alkyl silane of formula (II). More preferably, the aminosiloxane/alkyl silane blend for imparting hydrophobicity to hair of the present invention, comprises 5 to 75 wt % (preferably, 10 to 70 wt %; more preferably, 40 to 60 wt %) of a cosmetically acceptable alkyl silane of formula (II)

(II)

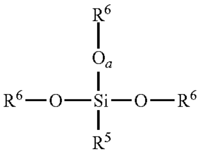

wherein a is selected from 0 and 1 (preferably, wherein a is a 1); wherein $R^5$ is a $C_{2-10}$ alkyl group with an addition reaction functional moiety; (preferably, wherein $R^5$ is a $C_{2-10}$ alkyl group with an addition reaction functional moiety selected from an epoxide group (e.g., glycidyl) and a vinyl group); and wherein each $R^6$ is independently selected from a $C_{1-4}$ alkyl group; (preferably, wherein each $R^6$ is independently selected from a $C_{1-3}$ alkyl group; more preferably, wherein each $R^6$ is independently selected from a $C_{1-2}$ alkyl group; most preferably, wherein each $R^6$ is an ethyl group).

Optionally, the $R^5$ group can be further substituted with an oxygen atom. For example, the $R^5$ group can include an oxygen forming an ether linkage within the $C_{2-10}$ alkyl group.

Optionally, the $R^5$ group is selected from a $C_{2-10}$ alkyl group, wherein the $C_{2-10}$ alkyl group can include a cyclic structure (e.g., a cyclohexyl ring).

Preferably, the aminosiloxane/alkyl silane blend for imparting hydrophobicity to hair of the present invention, comprises a cosmetically acceptable polydimethylsiloxane of formula (III). More preferably, the aminosiloxane/alkyl silane blend for imparting hydrophobicity to hair of the present invention, comprises 15 to 93.8 wt % (preferably, 20 to 88 wt %; more preferably, 25 to 57 wt %) of a cosmetically acceptable polydimethylsiloxane of formula (III)

(III)

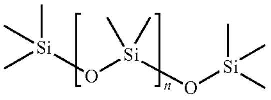

wherein n is an average of 0 to 150 (preferably, 0 to 100; more preferably, 0 to 50; still more preferably, 0 to 25; most preferably, 0 to 8).

Preferably, in preparing the aminosiloxane/alkyl silane blend for imparting hydrophobicity to hair of the present invention, the cosmetically acceptable polydimethylsiloxane of formula (III) is blended with the cosmetically acceptable alkyl silane of formula (II) and the cosmetically acceptable condensation catalyst with moderate agitation (e.g., mechanical stirring) until uniform. Then the cosmetically acceptable aminosiloxane of formula (I) is slowly added to the system with continued agitation until uniform. While not mandatory, it is preferred to prepare the aminosiloxane/alkyl silane blend in an inert atmosphere (e.g., nitrogen).

The aminosiloxane/alkyl silane blend for imparting hydrophobicity to hair of the present invention may be used as provided to treat hair. Alternatively, the aminosiloxane/alkyl silane blend for imparting hydrophobicity to hair of the present invention may be used as an additive for incorporating into a formulated hair care system to provide that system with the ability to impart hydrophobicity to hair.

Some embodiments of the present invention will now be described in detail in the following Examples.

Comparative Examples C1-C2 and Examples 1-4: Aminosiloxane/alkyl silane Blends A blend was prepared having the composition of components noted in Table 1 for each of Comparative Examples C1-C2 and Examples 1-4.

TABLE 1

| | Example (wt %) | | | | | |
|---|---|---|---|---|---|---|
| Component | Comp. Ex. C1 | Comp. Ex. C2 | Ex. 1 | Ex. 2 | Ex. 3 | Ex. 4 |
| Condensation catalyst[1] | 6 | 6 | 6 | 6 | 6 | 6 |
| non-addition reactive alkyl silane[2] | 50 | — | — | — | — | — |
| addition reactive alkyl silane[3] | — | — | 50 | — | — | — |
| addition reactive alkyl silane[4] | — | — | — | 50 | 50 | 50 |
| Aminosiloxane[5] | — | — | — | 10 | — | — |
| Aminosiloxane[6] | — | — | — | — | 10 | — |
| Aminosiloxane[7] | 10 | 10 | 10 | — | — | 10 |
| Polydimethylsiloxane[8] | 34 | 84 | 34 | 34 | 34 | 34 |

[1]TYZOR ® TnBT organic titanate (tetra-n-butyl titanate) available from Dorf Ketal.
[2]XIAMETER ® OFS-6381 alkyl functional silane available from The Dow Chemical Company.
[3]XIAMETER ® OFS-6106 glycidoxi functional silane available from The Dow Chemical Company.
[4]XIAMETER ® OFS-6518 vinyl functional silane available from The Dow Chemical Company
[5]DOWSIL ™ 2-8566 conditioning agent (INCI: Amodimethicone) available from The Dow Chemical Company.
[6]DOWSIL ™ 8500 conditioning agent (INCI: Bis ($C_{13-15}$ alkoxy) PG-Amodimethicone) available from The Dow Chemical Company.
[7]DOWSIL ™ AP-8087 conditioning agent (INCI: Bis-Hydroxy/Methoxy Amodimethicone) available from The Dow Chemical Company.
[8]DOWSIL ™ PMX 200/2 fluid (INCI: Dimethicone) available from The Dow Chemical Company.

Hair Hydrophobicity

The blends prepared according to each of Comparative Examples C1-C2 and Examples 1-4 were tested on two separate 3 g hair samples (Slightly Bleached Caucasian Hair, International Hair Importers, Inc.). The hair samples were first rinsed with water for 30 seconds. Then a 9% w/w aqueous solution of sodium lauryl ether sulfate was massaged into the hair samples for 30 seconds. Then the hair samples were rinsed with water for 30 seconds. Finally, the blends prepared according to Comparative Examples C1-C2 and Examples 1-4 were diluted with polydimethylsiloxane (DOWSIL™ PMX 200/2 fluid) to provide 20 wt % of each blend in PDMS. The diluted blends were then added to separate hair samples at the dosage (g of diluted blend/g of hair) as noted in TABLE 2 and massaged in to the hair for 30 seconds. The hair samples where then rinsed with water for 30 seconds and dried before hydrophobicity testing. The water used for rinsing in this testing was softened to a hardness of 80 ppm and heated to 38 °C.

To measure hydrophobicity of the hair, the tresses were combed straight and the tresses were held tightly on both ends with a holder. Ten drops of water were placed at different locations on each tress from the root to the tip. Measurements of the water contact angle at each drop were taken ten seconds after the drop of water got in contact with the tress. The higher the angle, the higher the hydrophobicity (which is desirable). This process was repeated for each of the tresses after washing 0, 5, 10, 20 and 30 times with a 9% w/w aqueous solution of sodium lauryl ether sulfate. The average contact angle is reported in TABLE 2.

TABLE 2

| | | Contact angle (in degrees) following the noted number of washes | | | | |
|---|---|---|---|---|---|---|
| Blend | Dosage | 0 | 5 | 10 | 20 | 30 |
| C1 | 0.15 | 100.5 | 13.7 | 35.7 | 0 | 0 |
| C1 | 0.30 | 94.9 | 91.2 | 35.7 | 17.9 | 0 |
| C2 | 0.15 | 121.7 | 7.4 | 0 | 0 | 0 |
| C2 | 0.30 | 130.2 | 98.3 | 65.3 | 0 | 0 |
| 1 | 0.15 | 31.0 | 111.5 | 101.4 | 102.4 | 70.9 |
| 1 | 0.30 | 107.0 | 117.2 | 109.0 | 110.3 | 84.3 |
| 2 | 0.15 | 123.6 | 110.4 | 93.3 | 91.7 | 65.6 |
| 2 | 0.30 | 121.7 | 112.5 | 90.9 | 95.9 | 42.4 |
| 3 | 0.15 | 131.1 | 112.1 | 73.1 | 41.1 | 23.8 |
| 3 | 0.30 | 122.7 | 111.2 | 104.5 | 93.0 | 33.7 |
| 4 | 0.15 | 128.9 | 108.6 | 93.3 | 40.6 | 43.7 |
| 4 | 0.30 | 132.9 | 114.9 | 102.9 | 100.3 | 45.6 |

Hair Coefficient of Friction

Coefficient of friction is an industry standard method of measuring reduced frictional properties of treatments on hair and correlates with sensory attributes for smoothness and softness. A Diastron MTT175 tensile tester with 50 g normal force mounted on rubber probe was used for testing in a temperature and humidity controlled room. Two tresses per treatment and five measurements per tress were tested to generate the average friction data reported in TABLE 3. Coefficient of friction (COF)=F/N, wherein F was the externally applied force and N was the normal force. The same tresses from the hydrophobicity study were used for measuring the coefficient of friction in the dry state.

TABLE 3

| | | COF following the noted number of washes | | | | |
|---|---|---|---|---|---|---|
| Blend | Dosage | 0 | 5 | 10 | 20 | 30 |
| C1 | 0.15 | 0.29 | 0.63 | 0.62 | 0.57 | — |
| C1 | 0.30 | 0.25 | 0.69 | 0.52 | 0.65 | — |
| C2 | 0.15 | 0.68 | 0.65 | — | — | — |
| C2 | 0.30 | 0.59 | 0.71 | 0.67 | — | — |
| 1 | 0.15 | 0.30 | 0.36 | 0.44 | 0.56 | 0.56 |
| 1 | 0.30 | 0.25 | 0.33 | 0.48 | 0.52 | 0.58 |
| 2 | 0.15 | 0.42 | 0.51 | 0.62 | 0.59 | 0.64 |
| 2 | 0.30 | 0.48 | 0.57 | 0.57 | 0.66 | 0.59 |
| 3 | 0.15 | 0.48 | 0.61 | 0.63 | 0.54 | 0.65 |
| 3 | 0.30 | 0.54 | 0.57 | 0.54 | 0.72 | 0.61 |
| 4 | 0.15 | 0.40 | 0.45 | 0.63 | 0.54 | 0.66 |
| 4 | 0.30 | 0.39 | 0.47 | 0.67 | 0.56 | 0.47 |

I claim:

1. An aminosiloxane/alkyl silane blend for imparting hydrophobicity to hair, consisting of:

(a) 0.2 to 15 wt % of a cosmetically acceptable condensation catalyst selected from the group consisting of organic titanates, organic zirconates and mixtures thereof;

(b) 1 to 20 wt % of a cosmetically acceptable aminosiloxane of formula (I)

(I)

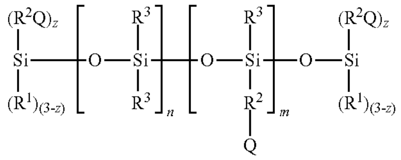

wherein each $R^1$ is independently selected from the group consisting of a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group;

wherein $R^2$ is a divalent alkylene radical having one to ten carbon atoms;

wherein each $R^3$ is independently selected from the group consisting of a $C_{1-30}$ alkyl group, a $C_{5-30}$ aryl group, a $C_{6-30}$ aralkyl group and a $C_{1-30}$ alkaryl group;

wherein Q is a monovalent radical selected from the group consisting of $—NR^4_2$ and $—NR^4(CH_2)_xNR^4_2$;

wherein each $R^4$ is independently selected from the group consisting of a hydrogen and a $C_{1-4}$ alkyl group;

wherein x is 2 to 6;

wherein z is 0 or 1;

wherein n is 25 to 3,000; and wherein m is 0 to 3,000;

with the proviso that at least 50 mol % of the total number of $R^1$ and $R^3$ groups are methyl and with the proviso that when m is 0, z is 1;

(c) 5 to 75 wt % of a cosmetically acceptable alkyl silane of formula (II)

(II)

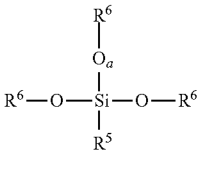

wherein a is selected from 0 and 1;

wherein $R^5$ is a $C_{2-10}$ alkyl group with an addition reaction functional moiety selected from an epoxide group and a vinyl group; and wherein each $R^6$ is independently selected from a $C_{1-4}$ alkyl group; and (d) 15 to 93.8 wt % of a cosmetically acceptable polydimethylsiloxane of formula (III)

(III)

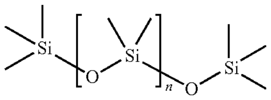

wherein n is an average of 0 to 150.

2. The aminosiloxane/alkyl silane blend of claim 1, wherein the addition reaction functional moiety is an epoxide group.

3. The aminosiloxane/alkyl silane blend of claim 1, wherein the cosmetically acceptable condensation catalyst is an organic titanate.

4. The aminosiloxane/alkyl silane blend of claim 1, wherein z is 0.

5. The aminosiloxane/alkyl silane blend of claim 4, wherein $R^2$ is selected from the group consisting of trimethylene, tetramethylene, pentamethylene, $—CH_2CH(CH_3)CH_2—$ and $—CH_2CH_2CH(CH_3)CH_2—$.

6. The aminosiloxane/alkyl silane blend of claim 1, wherein a is 1.

7. The aminosiloxane/alkyl silane blend of claim 1, wherein the aminosiloxane/alkyl blend consists of:

1 to 8 wt % of the cosmetically acceptable condensation catalyst;

2 to 15 wt % of the cosmetically acceptable aminosiloxane of formula (I);

40 to 60 wt % of the cosmetically acceptable alkyl silane of formula (II); and 25 to 57 wt % of the cosmetically acceptable polydimethylsiloxane of formula (III).

8. The aminosiloxane/alkyl silane blend of claim 7, wherein the cosmetically acceptable condensation catalyst is a organic titanate; wherein z is 0 and wherein the addition reaction functional group is selected from the group consisting of an epoxide group and a vinyl group.

9. The aminosiloxane/alkyl silane blend of claim 8, wherein $R^2$ is selected from the group consisting of trimethylene, tetramethylene, pentamethylene, $—CH_2CH(CH_3)CH_2—$ and $—CH_2CH_2CH(CH_3)CH_2—$.

10. The aminosiloxane/alkyl silane blend of claim 9, wherein a is 1.

* * * * *